United States Patent [19]
Corrigan et al.

[11] Patent Number: 5,945,529
[45] Date of Patent: Aug. 31, 1999

[54] SYNTHESIS OF POLYOL FATTY ACID POLYESTERS USING COLUMN WITH INERT GAS STRIPPING

[75] Inventors: Patrick Joseph Corrigan, Hamilton County; Corey James Kenneally, Warren County; Eric Paul Granberg, Hamilton County, all of Ohio

[73] Assignee: The Procter & Gamble Company, Cincinnati, Ohio

[21] Appl. No.: 08/683,899

[22] Filed: Jul. 19, 1996

[51] Int. Cl.$^6$ .......................... C07C 67/03; C07H 13/06
[52] U.S. Cl. .............................. 536/119; 554/168
[58] Field of Search .............................. 536/119; 554/168

[56] References Cited

U.S. PATENT DOCUMENTS

| | | | |
|---|---|---|---|
| 3,347,848 | 10/1967 | Ismail et al. | 536/119 |
| 3,353,966 | 11/1967 | Hugenberg et al. | 426/610 |
| 3,714,144 | 1/1973 | Feuge et al. | 536/119 |
| 3,963,699 | 6/1976 | Rizzi et al. | 536/119 |
| 4,032,702 | 6/1977 | James | 536/119 |
| 4,298,730 | 11/1981 | Galleymore et al. | 536/119 |
| 4,334,061 | 6/1982 | Bossier, III | 536/119 |
| 4,348,540 | 9/1982 | Ferris et al. | 568/472 |
| 4,517,360 | 5/1985 | Volpenhein | 536/119 |
| 4,518,772 | 5/1985 | Volpenhein | 536/119 |
| 4,773,881 | 9/1988 | Nieuwenhuis et al. | 536/119 |
| 4,806,632 | 2/1989 | McCoy et al. | 536/124 |
| 5,043,438 | 8/1991 | Buter | 536/119 |
| 5,158,796 | 10/1992 | Bernhardt et al. | 426/549 |
| 5,231,199 | 7/1993 | Willemse | 554/174 |
| 5,596,085 | 1/1997 | Silver et al. | 536/18.6 |
| 5,648,483 | 7/1997 | Granberg et al. | 536/119 |

FOREIGN PATENT DOCUMENTS

| | | |
|---|---|---|
| 0349059 | 1/1990 | European Pat. Off. |
| 50-135016 | 10/1975 | Japan . |
| 2109265 | 6/1981 | United Kingdom . |
| WO9204360 | 3/1992 | WIPO . |
| WO9311141 | 6/1993 | WIPO . |

OTHER PUBLICATIONS

Journal of the American Chemists' Society, "A Solvent–Free Synthesis of Sucrose Polyesters," George P, Rizzi and Harry M. Taylor, Apr. 1978, see pp. 398–401.

Prentice–Hall International Series in the Physical and Chemical Engineering Sciences, "Basic Principles and Calculations in Chemical Engineering, Second Edition" David M. Himmelblau, 1967, see pp. 96–97.

O. Levenspiel, "Chemical Reaction Engineering," John Wiley & Sons, New York (1972), see pp. 124–139.

Journal of the American Chemists' Society, vol. 47, "Preparation of Sucrose Esters by Interesterification," R.O. Feuge et al., see pp. 56–60, 1969.

*Primary Examiner*—Richard L. Raymond
*Attorney, Agent, or Firm*—Dinsmore & Shohl LLP

[57] ABSTRACT

Processes for the synthesis of polyol fatty acid polyester by transesterification of a polyol comprise reacting polyol with a first portion of fatty acid lower alkyl ester to provide a first step reaction product in which substantially all of the polyol is reacted with at least one fatty acid lower alkyl ester. The processes then employ a multistage column providing substantial plug flow of liquid therein for further transesterification of the first step reaction product. Partially esterified polyol, a second portion of fatty acid lower alkyl ester and catalyst are fed to the column to form a mixture and cause further transesterification of the partially esterified polyol and fatty acid lower alkyl ester, with lower alkyl alcohol being formed as a by product. The resulting liquid mixture of reactants and product is passed in a first direction between adjacent stages through the column for further reaction of partially esterified polyol with fatty acid lower alkyl ester. An inert stripping or sparging gas is fed through the column in a second direction between adjacent stages, counter current to the flow of the liquid mixture between adjacent stages in the first direction, with radial shear agitation. The lower alkyl alcohol by-product of the polyol-fatty acid lower alkyl ester reaction is transferred from the liquid mixture to the inert gas.

38 Claims, 1 Drawing Sheet

SYNTHESIS OF POLYOL FATTY ACID POLYESTERS USING COLUMN WITH INERT GAS STRIPPING

FIELD OF THE INVENTION

The present invention is directed to processes for the synthesis of polyol fatty acid polyesters by transesterification of a polyol, which processes are effected in a multistage column providing plug flow of materials therethrough and using inert gas stripping. More specifically, the present invention is directed to such processes wherein partially esterified polyol and fatty acid lower alkyl ester are provided to a multistage column in which liquid reactants and product flow through the column counter-current to a stripping or sparging gas which removes alcohol by-product from the liquid in each stage.

BACKGROUND OF THE INVENTION

Processes for the synthesis of polyol fatty acid polyesters by the transesterification of a polyol are well known in the art. For example, the Rizzi et al. U.S. Pat. No. 3,963,699 discloses a solvent-free transesterification process comprising two main steps, each of which is conducted in a batch reactor. In the first step, a mixture of polyol, a fatty acid lower alkyl ester, an alkali metal fatty acid soap, and a basic catalyst are heated to form a homogenous melt of partially esterified polyol and unreacted starting materials. In a second step, excess fatty acid lower alkyl esters are added to the reaction product of the first step to form the polyol fatty acid polyester. Rizzi et al. further disclose that a lower alcohol is formed as by-product of the reaction and, in order to promote the reaction, the alcohol by-product is preferably removed. Many removal techniques are acknowledged by Rizzi et al. as being known in the art; Rizzi et al. indicate that vacuum removal, both with and without an inert gas sparging, has been found to promote the reaction, and that simple distillation under atmospheric pressure may also be sufficient.

The Volpenhein U.S. Pat. Nos. 4,517,360 and 4,518,772 disclose further solvent-free transesterification processes for producing higher polyol fatty acid polyesters. In U.S. Pat. No. 4,517,360, Volpenhein discloses the use of potassium carbonate, sodium carbonate or barium carbonate as a catalyst and the use of a fatty acid methyl, 2-methoxy ethyl or benzyl ester. In U.S. Pat. No. 4,518,772, Volpenhein discloses the use of preferred molar ratios of soap to polyol of from about 0.6:1 to about 1:1 in the first step of the two step process. Volpenhein also employs a batch reaction process and discloses the advantage of removing lower alcohol by-product to promote the transesterification reaction.

The Buter U.S. Pat. No. 5,043,438 discloses a process for the synthesis of polyol fatty acid esters by reacting a polyol and a fatty acid lower alkyl ester under substantially solvent-free conditions. Buter discloses that the process employs a prereactor in which the reaction mixture is in steady state with mass-balanced in-going reactant streams and out-going product streams having a polyol conversion of 1% or more, and a nonagitated column main reactor, which in the examples was a three-tray column reactor with counter-current stripping. Buter further discloses that the process reduces initial viscosity and/or de-mixing problems caused by the heterogeneous nature of the reactant mixture and by the use of soap emulsifiers. However, the process disclosed by Buter is not suitable for use on an industrial scale owing to the large quantities and high flow rate of stripping gas, i.e. nitrogen, and large reaction times which would be required therein.

Polyol fatty acid polyesters are increasingly being employed in various applications. Particularly, there has been a significant increase in the use of polyol fatty acid polyesters as low-calorie fats in many food products. Accordingly, the demand for polyol fatty acid polyesters suitable for human consumption is rapidly increasing. As a result, processes for more efficient and economical synthesis of polyol fatty acid polyesters are necessary and desirable.

SUMMARY OF THE INVENTION

Accordingly, it is an object of the present invention to provide novel processes for the synthesis of polyol fatty acid polyesters, particularly by the transesterification of polyol reactant. It is a further object of the invention to provide processes for the synthesis of polyol fatty acid polyesters, which processes may be practiced on an industrial or commercial scale. It is a related object to provide processes for the synthesis of polyol fatty acid polyesters, which processes have improved efficiency and/or are more economical as compared with various conventional processes for the production of polyol fatty acid polyesters.

These and additional objects are provided by the processes according to the present invention which are directed to the synthesis of polyol fatty acid polyesters by solvent-free transesterification of polyol. In accordance with the present invention, polyol is reacted with a first portion of fatty acid lower alkyl ester to provide a first step reaction product in which substantially all of the polyol is reacted with at least one fatty acid lower alkyl ester. The first step reaction product is then provided to a multistage column, together with a second portion of fatty acid lower alkyl ester. The first step reaction product and fatty acid lower alkyl ester react throughout the column to form a liquid mixture comprising substantially completely esterified polyol, fatty acid lower alkyl ester and lower alkyl alcohol by-product. Each segment or stage of the multistage column is separated from an adjacent prior segment or stage by a segment plate and each segment plate is provided with at least one passage for allowing transfer of a liquid in a first direction between adjacent stages and with at least one passage allowing transfer of gas in a second direction between adjacent stages, with the second direction being counter current to the first direction.

In accordance with an important feature, the multistage column provides for plug flow of materials therethrough. The liquid mixture is passed in the first direction between adjacent stages through the column, whereby further reaction of partially esterified polyol with fatty acid lower alkyl ester occurs, and an inert gas is fed through the column in the second direction between adjacent stages, counter current to the flow of the liquid mixture between adjacent stages in the first direction. Agitation providing radial shear increases gas-liquid contact between the inert gas and the liquid mixture in each state of the column. The present inventors have discovered that the plug flow of materials provided by the multistage column, together with the provision of the inert stripping gas with radial shear agitation, provides a significant increase in gas-liquid contact. As a result, the lower alkyl alcohol by-product of the polyol-fatty acid lower alkyl ester reaction is transferred from the liquid mixture to the inert gas, thereby promoting further transesterification reaction of polyol and partially esterified polyol with fatty acid lower alkyl ester.

The processes according to the present invention provide several important advantages. First, the processes maximize contact between the inert gas and the liquid mixture of reactants and product. As a result, the lower alkyl alcohol by-product resulting from the transesterification reaction is more readily transferred to the inert gas, whereby further transesterification reaction is more fully promoted. This, in turn, allows the use of lower amounts of inert gas per pound of reacting feed and provides shorter reaction times to reach a desired conversion, as compared with many conventional processes. Additionally, the transesterification reaction in the processes of the present invention may be run at atmospheric pressure or super atmospheric pressure, rather than under the vacuum which has been commonly employed in conventional methods. Use of atmospheric or superatmospheric pressure during the transesterification reaction allows more efficient removal and recovery of the lower alkyl alcohol by-product during later processing of the inert gas. The present processes therefore provide efficient production of polyol fatty acid polyesters and significant savings in manufacturing and equipment costs.

These and additional advantages will be more fully understood in view of the following detailed description.

BRIEF DESCRIPTION OF THE DRAWING

The processes of the present invention, and the advantages thereof, will be more fully apparent in view of the accompanying drawing in which.

DETAILED DESCRIPTION

Figure 1:
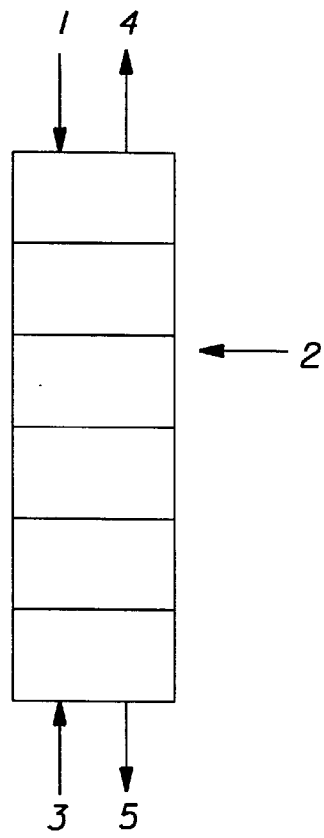
FIG. 1 is a schematic diagram of one embodiment of a multistage column suitable for use according to the present invention.

The processes according to the present invention relate to the synthesis of polyol fatty acid polyester by the solventless transesterification of polyol. As used herein, the term "polyol" is intended to include any aliphatic or aromatic compound containing at least two free hydroxyl groups. In practicing the processes disclosed herein, the selection of a suitable polyol is simply a matter of choice. For example, suitable polyols may be selected from the following classes: saturated and unsaturated straight and branched chain linear aliphatic; saturated and unsaturated cyclic aliphatic, including heterocyclic aliphatic; or mononuclear or polynuclear aromatics, including heterocyclic aromatics. Carbohydrates and non-toxic glycols are preferred polyols. Monosaccharides suitable for use herein include, for example, mannose, galactose, arabinose, xylose, ribose, apiose, rhamnose, psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol.

Particularly preferred classes of materials suitable for use herein include the monosaccharides, the disaccharides and sugar alcohols. Preferred carbohydrates and sugar alcohols include xylitol, sorbitol and sucrose. Sugar ethers and alkoxylated polyols, such as polyethoxy glycerol can also be used herein.

The fatty acid lower alkyl esters which are employed as reactants in the present processes include the methyl and ethyl esters of fatty acids containing about eight or more carbon atoms, and preferably containing from 8 to about 22 carbon atoms, and mixtures of such esters. Suitable esters can be prepared by the reaction of diazoalkanes and fatty acids, or derived by alcoholysis from the fatty acids naturally occurring in fats and oils. Fatty acid esters suitable for use herein may be derived from either saturated or unsaturated fatty acids. Suitable preferred saturated fatty acids include, for example, capric, lauric, palmitic, stearic, behenic, isomyristic, isomargaric, myristic, caprylic, and anteisoarachadic. Suitable preferred unsaturated fatty acids include, for example, maleic, linoleic, licanic, oleic, linolenic, and erythrogenic acids. Mixtures of fatty acids derived from soybean oil, palm oil, coconut oil, cottonseed and fatty hydrogenated rapeseed oil are especially preferred for use herein. Methyl esters are the preferred fatty acid esters for use herein, since their use in the processes herein tends to result in high yields of polyol fatty acid polyesters.

A catalyst is preferably employed in the processes of the present invention. The catalyst may be any one of a number of basic catalysts known in the art for use in the transesterification of polyol. Preferably, the catalyst is selected from the group consisting of alkali metals, including sodium, lithium or potassium, other metals such as calcium or aluminum, alloys of two or more of these metals, or compounds of these metals, including but not limited to, carbonates, bicarbonates, alkoxides, or hydroxides of these metals, or mixtures thereof. In a further preferred embodiment of the present processes, the basic catalyst is a carbonate, bicarbonate, alkoxide or hydride of sodium or potassium, or comprises mixtures of two or more of these compounds. Preferably, the catalyst is employed both in the initial reaction of the polyol with the first portion of fatty acid lower alkyl ester, and in the subsequent reaction of the first step reaction product of partially esterified polyol with the second portion of the fatty acid lower alkyl ester which is conducted in the multistage column.

The initial reaction of the polyol and the first portion of the fatty acid lower alkyl ester may be conducted in accordance with procedures known in the art, for example as employed in the first steps of the methods taught in the Rizzi et al. U.S. Pat. No. 3,963,699 and the Volpenhein U.S. Pat. Nos. 4,517,360 and 4,518,772, all of which are incorporated herein by reference. The amounts of polyol and fatty acid lower alkyl ester reactants, catalyst and emulsifier, if employed, used in the initial transesterification reaction of polyol with the first portion of the fatty acid lower alkyl ester may be those conventionally employed by Rizzi et al, Volpenhein and others in the art. In preferred embodiments, the initial reaction of polyol and the first portion of fatty acid alkyl ester employs a polyol:fatty acid lower alkyl ester molar ratio of from about 1:3 to about 1:7, with a ratio of about 1:5 being particularly preferred. The molar ratio of polyol to catalyst is preferably in the range of from about 1:0.01 to about 1:0.5, with a molar ratio of about 1:0.1 being preferred.

As is well known in the art, the initial reaction of the polyol with the first portion of the fatty acid lower alkyl ester may be conducted in the presence of an emulsifier. The emulsifier assists in overcoming the incompatibility of the polyol and the fatty acid lower alkyl ester reactants which is a result of the heterogeneous nature of the reactants. Suitable emulsifiers include alkali metal fatty acid soaps, including alkali metal salts of saturated and unsaturated fatty acids having at least about 8 carbon atoms, and preferably from about 8 to about 18 carbon atoms. Accordingly, suitable alkali metal fatty acid soaps include, but are not limited to, the lithium, sodium, potassium, rubidium and cesium salts of fatty acids such as capric, lauric, myristic, palmitic, licanic, parinaric and stearic acids. Mixtures of fatty acids derived from soybean oil, sunflower oil, safflower oil and corn oil are preferred for use in the alkali metal soaps. Alternatively, or in addition to the alkali metal soaps, partially esterified polyol may be employed to solubilize the polyol and thereby transfer the polyol into a liquid phase together with the fatty acid lower alkyl ester reactant. The emulsifier is preferably used in an amount sufficient to provide a polyol:emulsifier molar ratio in a range of from about 1:0.01 to about 1:1.

The reaction is conducted until substantially all of the polyol is reacted with at least one fatty acid lower alkyl ester, i.e. at least one hydroxy group on substantially all of the polyol molecules has been esterified. Preferably, the reaction product of this initial or fist step of the reaction contains less than about 2 weight percent of unreacted polyol, i.e., polyol in which none of the hydroxy groups are esterified, and more preferably less than about 1 weight percent of unreacted polyol, and most preferably less than about 0.5%. The reaction product of this first step will typically comprise lower ester products. For example, in a preferred embodiment wherein the polyol is sucrose, the first step reaction product typically comprises mono, di, tri and tetra esters of the polyol. The degree of conversion of the polyol, i.e., the percentage of polyol hydroxyl groups converted to ester groups, in the first step reaction product is preferably in the range of from about 15 to about 60 percent, and more preferably is at least about 25 percent, and more preferably is about 50 percent.

Lower alkyl alcohol by-product from the initial transesterification reaction should be removed to increase the rate of reaction. While the reaction will proceed if the alcohol by-product remains in the reaction mixture at this state, the reaction rate is lower. In a preferred embodiment, the lower alkyl alcohol by-product is removed, for example by conducting the initial reaction under vacuum or by providing inert gas sparging or stripping in the reactor.

Preferably, the initial reaction of the polyol and the first portion of the fatty acid lower alkyl ester is conducted in any type of reactor which allows some back mixing of product with reactants. Back mixing of partially esterified polyol product with the polyol reaction allows solubilization of the polyol reactant, and the faster the polyol is transferred to the liquid phase where it is available for reaction with the fatty acid lower alkyl ester, the faster this stage of the reaction will proceed to completion.

To obtain the desirable back mixing, the initial transesterification may be conducted in a batch reactor as employed by Rizzi et al. and others. Alternatively, the initial transesterification may be conducted in one or more continuous stirred tank reactors arranged in series. Preferably, one or two continuous stirred tank reactors are employed for this initial reaction. When two continuous stirred tank reactors are employed, it is preferred that the output product from the first reactor contains not greater than about 5 weight percent, and more preferably not greater than about 2 weight percent, unreacted polyol.

In a further alternative embodiment, the initial transesterification may be conducted in a multistage column reactor which allows some back mixing between reactants and product. The multistage column reactor may be separate from or form a part of the multistage column reactor employed in the subsequent step of the present processes, although the multistage column employed in the subsequent step of the present processes provides plug flow and avoids back mixing, as will be discussed in further detail below. When a multistage column providing back mixing is employed for the initial reaction of polyol, from about two to about six stages of a multistage column are particularly suitable for conducting the initial transesterification reaction of polyol and the first portion of fatty acid lower alkyl ester. One of ordinary skill in the art will recognize that if a column reactor is employed for the initial transesterification reaction, one or more steps must be taken to prevent solid polyol reactant from interfering with operation of the column. For example, solid polyol reactant may be emulsified and/or solubilized with partially esterified polyol prior to introduction of the polyol into the column. Alternatively, the first stage of the column into which the polyol is introduced can be provided with filter means or the like which prevent solid material from being transferred to a subsequent stage of the column.

In accordance with an important feature of the invention, the first step reaction product is then provided, together with a second portion of fatty acid lower alkyl ester, to a multistage column for further transesterification. As discussed above, it is well known in the art that the transesterification reaction of the polyol with a fatty acid lower alkyl ester results in the formation not only of the polyol fatty acid polyester, but also in the formation of a lower alkyl alcohol by-product. When fatty acid methyl esters are employed as reactants, the lower alkyl alcohol by-product comprises methanol. It is also well known in the art that removal of the lower alkyl alcohol by-product such as methanol promotes further transesterification reaction, particularly in the later stages of reaction as the higher esters of a polyol such as sucrose are produced. In the present processes, improved removal of the lower alkyl alcohol during the transesterification reaction is achieved.

More particularly, the synthesis of the polyol fatty acid polyester product from the first step reaction product is effected in a multistage column. A schematic diagram of a suitable multistage column is shown in FIG. 1. As demonstrated in FIG. 1, the first step reaction product comprising partially esterified polyol and a second portion of fatty acid ester reactant are fed to the column, together with the catalyst, shown schematically by arrow 1. The reactants for the further transesterification reaction may be provided to the column individually or separately, and then mixed therein, or alternatively, the reactants may be supplied together in one or more common inlet streams. The entire amount of the fatty acid lower alkyl ester for the remainder of the transesterification reaction may be fed directly into the first stage of the column, together with the partially esterified polyol first step reaction product and the catalyst. Alternatively, a third portion of the fatty acid lower alkyl ester may be fed into the column at one or more stages which are intermediate to the ends of the column, shown schematically in FIG. 1 by arrow 2, thereby providing additional ester reactant for reaction with partially esterified polyol which is intermediate the ends of the column. The second and any additional portions of fatty acid alkyl ester which are added to the column are provided in an amount which, combined with the first potion of fatty acid alkyl ester employed in the initial stage, provides a total molar ratio of ester groups to polyol hydroxyl groups of greater than 1. When the polyol comprises sucrose and the fatty acid alkyl ester is a monoester, the molar ratio of total ester to sucrose is preferably at least 10:1.

Similarly, the catalyst may be supplied separately to the column, or alternatively, the catalyst may be combined with one or both of the partially esterified polyol and fatty acid ester reactants prior to their introduction into the column.

An inert gas is also fed through the column, preferably to a location remote from the reactants' inlets. For example, as shown schematically by arrow 3 in FIG. 1, the inert gas is preferably fed to the end of the column opposite that to which the reactants and catalysts are supplied, thereby providing counter-current flow between the inert gas and liquids within the column. As further shown schematically by arrow 4 in FIG. 1, the inert gas containing the alcohol by-product resulting from reaction of the partially esterified polyol and fatty acid lower alkyl ester is removed from the column, separate from removal of the liquid polyol polyester reaction product shown in FIG. 1 by arrow 5. While concurrent flow between the inert gas and liquids in the column may be employed, counter-current flow is preferred as it provides increased efficiency in removal of the lower alkyl alcohol by-product.

For purposes of illustration only, the column shown in FIG. 1 has six segments or stages. In practice, the number of stages can be varied depending on the specific reactants, catalysts, reaction conditions and degree of conversion desired for the polyol polyester product. In practice, the present inventors have determined that a column having from 3 to about 18 segments or stages, preferably about four to six stages, is suitable for production of higher polyol fatty acid polyesters.

Figure 2:
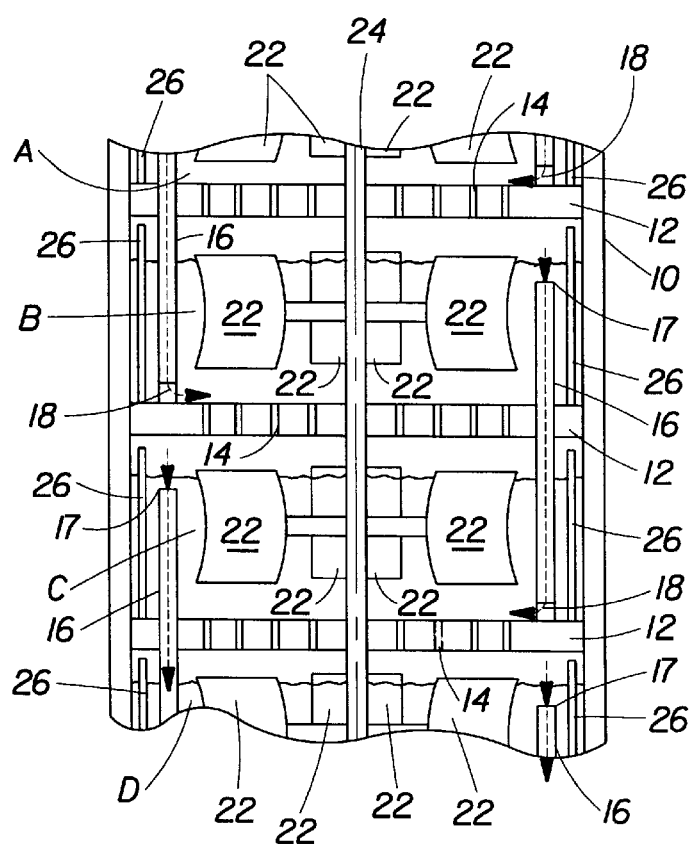
FIG. 2 is a schematic cross-sectional diagram of a portion of another embodiment of a multistage column suitable for use according to the present invention.

In the multistage column employed in the present processes, each segment or stage is separated from an adjacent prior stage by a segment plate, and each segment plate is provided with at least one passage allowing transfer of a liquid in a first direction between adjacent stages and with at least one passage allowing transfer of a gas in a second direction between adjacent stages, with the second direction being counter current to the first direction. While not required, it is preferred that the passages prevent transfer of solids between adjacent stages. One embodiment of a multistage column suitable for use in the present processes is shown in schematic cross section in FIG. 2. With reference to FIG. 2, the illustrated portion of the column 10 is shown having a plurality of stages A, B, C, D. The respective stages are separated from one another by a segment plate 12. In the embodiment of FIG. 2, each segment plate is provided with perforations or sieve holes 14 which allow the upward passage of the inert gas therethrough and provide for transfer of gas between adjacent stages. The pressure and/or flow rate of the inert gas moving through the column prevents transfer of liquids or solids between adjacent stages through the sieve holes 14.

The passage allowing transfer of liquid between adjacent stages of the multistage column shown in FIG. 2 comprises a series of overflow/downcomer tubes 16 provided with inlets 17 and outlets 18. More specifically, as the liquid in one stage reaches the height at which the inlet 17 of the overflow portion of the tube 16 is positioned, liquid flows through the overflow portion of the tube 16 down through the segment plate to the downcomer portion of tube 16 which is provided with an outlet 18 in the adjacent stage. The overflow tubes 16 may be provided with a filter screen or the like at their inlet 17 in order to prevent any solids, for example undissolved polyol, from passing therethrough. As shown in FIG. 2, the outlet 18 of the downcomer tube is preferably positioned in the lower area of the stage, thereby increasing the time for liquid-gas contact occurring within each stage as liquid flows upwardly in each stage to the overflow tube inlet. As also illustrated in FIG. 2, it is preferred that the overflow/downcomer tubes of adjacent stages are positioned remote from one another, thereby increasing the distance between the downcomer outlet 18 and the overflow inlet 17 in a particular stage. This arrangement contributes to increase gas-liquid contact in the column. The overflow/downcomer tubes may be located internal or external to the column.

As will be appreciated, the size of the sieve holes 14, the number of sieve holes 14 and the pattern of sieve holes 14 may be varied depending on the desired inert gas flow between adjacent stages. Similarly, the height of the overflow portion of tubes 16, the length of the downcomer portion of tubes 16 and the shape and position of the overflow/downcomer tubes 16 may also be varied within the scope of the present processes.

In an alternate embodiment to that shown in FIG. 2, each segment plate may be provided with restrictive holes. The column may be operated to limit the flow of gas in one direction and liquid in the opposite direction while permitting the flow of liquid in the one direction and the flow of gas in the opposite direction. Additional passages allowing transfer of a liquid in a first direction and gas in a second direction between adjacent stages, are known in the art and suitable for use in the multistage column employed in the present processes.

The multiple stages of the column employed in the present processes provide plug flow of liquid and gas throughout the column, as the segment plates restrict both forward and back mixing of gas and liquid. The present inventors have discovered that the plug flow provided by the multistage column of the present invention, in combination with the radial shear provided by agitation in the column, facilitates significantly increased removal of the alcohol by-product of the transesterification reaction, and therefore promotes further transesterification reaction. As a result, the plug flow achieved according to the present invention is advantageous for providing high conversion of the partially esterified polyol first step product to the desired polyol fatty acid polyesters.

In a preferred embodiment of the present processes, the first step reaction product of partially esterified polyol, the second portion of fatty acid lower alkyl ester and catalyst are fed to one end of the column to form a mixture and cause further transesterification of the partially esterified polyol with fatty acid lower alkyl ester, with lower alkyl alcohol being formed as a by-product. The resulting liquid mixture of reactants and product are then passed in the first direction (downwardly in the embodiment of FIG. 2) between adjacent stages through the column, whereby further reaction of partially esterified polyol with fatty acid lower alkyl ester occurs. The inert sparging or stripping gas is fed through the column in the second direction (upwardly in the embodiment of FIG. 2) between adjacent stages, with radial shear agitation in each stage, and counter current to the flow of the liquid mixture between adjacent stages in the first direction. Lower alkyl alcohol by-product resulting from the polyol fatty acid lower alkyl ester reaction is transferred from the liquid mixture to the inert gas. Removal of the lower alkyl alcohol by-product promotes further reaction of partially esterified polyol with fatty acid lower alkyl ester.

Any inert gas having a suitable partial pressure sufficient to affect transfer of the lower alkyl alcohol from the liquid phase to the gas phase may be employed. Particularly preferred inert gases for use in the processes of the present invention include nitrogen and aliphatic hydrocarbons, for example, hexane.

In order to maximize the gas-liquid contact surface area, and in turn maximize mass transfer of the lower alkyl alcohol by-product from the liquid reactant-product mixture to the inert gas, the inert gas is provided with agitation creating radial shear within one or more stages, preferable every stage, of the column. It has been discovered that the combination of the plug flow within the column and the radial shear agitation reduces the size of the inert gas bubbles within the liquid mixture and provides increased gas-liquid contact of the stripping gas and the liquid mixture containing the alcohol by-product. As a result, the amount of alcohol by-product transferred to the inert gas is significantly increased. Specifically, the partial pressure of the lower alkyl alcohol by-product, i.e. methanol, is reduced according to the present processes, thereby promoting transfer of the alcohol from the liquid mixture to the inert gas. Preferably, the partial pressure of the alcohol, i.e., methanol, in the final stage of the multistage column is reduced to less than about 10 mm Hg, more preferably less than about 5 mm Hg, and most preferably less than about 2 mm Hg, by the incoming inert gas. According to the present processes, the amount of nitrogen gas necessary to promote the reaction to the desired degree of completion may typically be reduced by about 2 fold to 4 fold, or even about 10 fold to about 100 fold for short reaction times, as compared with prior processes employing a series of continuous stirred tank reactors or a column without radial shear agitation. Suitable weight ratios of inert gas to liquid reactant feed to the column are in the range of less than about 4:1, preferably less than about 3:1, more preferably less than about 2.5:1, and most preferably not greater than about 2:1.

The column is preferably provided with at least one agitator in each stage of the column. More preferably, each stage of the column is provided with at least one agitator providing radial shear to increase contact surface area between the liquid mixture and the inert gas. It is also preferred that axial shear within each segment or stage of the column is minimized. The agitators in each segment or stage of the column therefore serve to disperse the inert gas into the liquid mixture and provide radial mixing. This reduces the average size of inert gas bubbles in the liquid, preferably to less than about 5 mm in diameter, more preferably to less than or equal to about 2 mm in diameter, and increases the amount of gas-liquid contact surface area which in turn, increases the efficiency of the mass transfer of the lower alkyl alcohol from the liquid mixture to the inert gas.

The agitation means is preferably in the form of impeller blades which are parallel to a drive shaft extending axially along the column. In the embodiment of the multistage column shown in FIG. 2, each segment or stage is provided with a plurality of impeller or agitator blades 22 which are arranged around a central axis 24. The central axis 24 rotates the agitator blades 22 to increase radial shear and consequently increase the contact surface area between the liquid reactant-product mixture and the inert stripping/sparging gas. The agitator or impeller blades may be curved or flat. The agitator blades 22 shown in the embodiment of FIG. 2 are curved in order to provide a lower aeration number. In a preferred embodiment, the agitator blades are concave in the direction of agitation, i.e. rotation. The radial shear agitation preferably results in an aeration number of less than about 2.0, and more preferably less than about 1.0. As demonstrated subsequently in the Examples, aeration number (Ae) is calculated as (inert gas volumetric flow rate)/(agitator speed)/(agitator diameter)$^3$. As will be appreciated, the number of blades per stage, the dimension and orientation of the blade surfaces and the position of the blades within each segment may be varied in order to increase radial shear within the stage and increase the surface area contact between the liquid mixture and the inert gas in each segment or stage of the column. Preferably, from about 4 to about 20 agitator blades are provided in each stage, more preferably from about 6 to about 12 agitator blades are provided in each stage.

In order to firther increase the gas dispersion in the liquid mixture, one or more segments or stages of the multistage column can be provided with one or more baffles extending between adjacent segment plates. Preferably each segment or stage of the multistage column is provided with a plurality of vertical baffles extending between adjacent segment plates defining the respective stage, with the baffles providing increased contact surface area between the liquid mixture and the inert gas within the stage. For example, in the embodiment of FIG. 2, a series of vertical baffles 26 are provided in each stage extending between adjacent segment plates. The baffles 26 are arranged near the outer perimeter of the segment plates. The present inventors have discovered that the combination of the vertical baffles and the blade agitators are particularly advantageous for providing increased radial shear of the inert gas in the liquid mixture and improving the transfer of the lower alkyl alcohol from the liquid mixture to the inert gas, thereby promoting the transesterification reaction.

The residence time for the reaction material in the multistage column according to the present processes is reduced as compared with conventional processes, thereby contributing to the efficiency of the present processes. Although residence time for the reaction materials will vary depending on the specific reactants and reactor parameters and conditions, in preferred embodiments of the present processes, particularly wherein the polyol is sucrose, residence times of less than about three hours are possible, and are preferably less than about two hours.

In order to affect and promote the transesterification reactions, both in the original transesterification of polyol and in the further transesterification in the multistage column, heat is preferably supplied to the reactions so that the reactions can be conducted at an elevated temperature in the range of from about 110° C. to about 180° C., more preferably from about 120° C. to about 150° C. In one embodiment, this elevated temperature can be provided by heating the contents of the respective reactors in situ. Alternatively, or in addition, one or more of the feed streams to the respective reactors may be preheated whereby polyol, fatty acid lower alkyl ester, partially esterified polyol and/or the inert gas are preheated to a temperature in the range of from about 120° C. to about 150° C. Heating can also be accomplished by providing sufficient power to the agitator drive to heat the liquid by frictional energy as it is agitated.

In conventional processes for the transesterification of polyol, the reactions have been conducted under vacuum conditions in order to facilitate removal of the lower alkyl alcohol by-product from the liquid polyol polyester product. As discussed above, the initial transesterification of polyol may similarly be conducted under vacuum. Additionally, while the further transesterification conducted in the multistage column according to the present process may similarly be conducted under vacuum conditions, the use of the multistage column and the present process steps allow the further transesterification reaction in the multistage column to be affected at atmospheric or super atmospheric pressures while maintaining the ability to remove the alcohol from the liquid product by use of the inert gas stripping or sparging stream provided with radial shear agitation. In fact, employment of atmospheric and super atmospheric pressures, rather than the vacuum conditions, in the multistage column are preferred for use in the present processes in order that the lower alkyl alcohol by-product may be more efficiently removed and recovered from the inert gas during later processing of the inert gas. As a result, recycle and reuse of the inert gas is facilitated. Accordingly, for conducting the presents methods, pressures at the top of the column are preferably in the range of from about 760 mm Hg to about 2500 mm Hg, more preferably from about 760 mm Hg to about 1100 mm Hg. One of ordinary skill in the art will recognize that the pressure at the bottom of the column will therefore be higher owing to the height of the column, liquid levels and changes in pressure resulting therefrom.

An additional advantage provided by the present processes employing a multistage column provided with agitation is that higher viscosity liquids can be utilized therein while still obtaining the desired gas-liquid contact and transfer of lower alkyl alcohol from liquid to inert gas. This is an especially important advantage in the production of sucrose fatty acid polyesters.

The processes of the present invention are particularly advantageous for producing polyol fatty acid polyester of a high degree of conversion. For example, the processes of the present invention may be used to affect at least 80%, more preferably greater than 90%, and in many cases greater than 95%, conversion of the hydroxyl groups of the polyol to ester groups. In a preferred embodiment of the invention, wherein the polyol is sucrose, the sucrose polyester product has a degree of conversion of greater than 95%, with at least 60 weight percent of the product, and more preferably at least 70 weight percent of the product, comprising the octaester. Optionally, partially esterified polyol product which is removed from the column in the desired product may be separated from the fully esterified product and recycled to the first stage or an intermediate stage of the column for further reaction with additional fatty acid lower alkyl ester reactant.

In accordance with conventional processes, the polyol fatty acid polyester product of the present processes may be subjected to washing, drying, bleaching, filtration, separation and/or deodorization processing steps and/or blended with other components for providing a final product.

In a further embodiment of the processes of the present invention, the inert gas containing the lower alkyl alcohol by-product is removed from the column and further processed to remove substantially all of the lower alkyl alcohol from the inert gas. Removal of substantially all of the lower alkyl alcohol from the inert gas requires that the partial pressure of the lower alcohol in the inert gas be reduced to less then about 10 mm Hg, preferably less than about 5 mm Hg, and most preferably less than about 2 mm Hg after this step. The inert gas with substantially all of the lower alkyl alcohol removed therefrom may then be recycled to the column. The lower alkyl alcohol may be removed from the inert gas using any of the conventional techniques known in the art. For example, the lower alkyl alcohol may be removed from the inert gas by cooling the inert gas which contains the alcohol, and passing the cooled product through an absorbent material, for example, carbon black, or the like, to absorb the alcohol from the gas.

The following examples are set forth to illustrate various features of the present processes. In both the examples and the remainder of the present specification, parts and percentages are by weight unless otherwise specified.

EXAMPLE 1

This example demonstrates one embodiment of the first stage of the reaction, i.e., the initial transesterification, which comprises reacting each polyol molecule, i.e. sucrose, with at least one fatty acid alkyl, i.e., methyl, ester molecule. The reactor system employed in this example comprises two stainless shell tank reactors in series, each 1.5 feet in diameter, and each having an agitator, a liquid level control system, a heater, a recirculation pump, and temperature and pressure sensors. The agitators are run at about 600 rpm. Sucrose, cottonseed fatty acid alkyl, i.e. methyl, esters, potassium stearate, and potassium carbonate are fed into the first reactor in the series at approximately the following molar ratios:

| Materials | Molar Ratio |
|---|---|
| Fatty acid methyl ester:sucrose | 5:1 |
| Potassium stearate (soap):sucrose | 0.2:1 |
| Potassium carbonate (catalyst):sucrose | 0.1:1 |

Both reactors are operated at about 135° C., and vacuum is applied to both reactors to maintain pressure at about 15 mm Hg. Both reactors act as continuous stirred tank reactors (CSTR's), i.e., the reactors are designed to have backmixing. As set forth above, backmixing is desirable in this stage of the reaction so that sucrose mono, di, and triester products of the reaction are maintained in intimate contact with incoming unreacted polyol. The sucrose mono-, di-, and triesters solubilize the solid sucrose into the reaction mixture, enabling it to react more readily with the fatty acid lower alkyl esters. The average residence time of the reaction mixture in the first reactor is about 1 hour. The reaction mixture is pumped from the first reactor to the second reactor at the same rate as the in-going feed material to the first reactor so that the content in the first reactor is maintained constant. The reaction material pumped into the second reactor has an average residence time of about 1.5 hours therein. Reaction material is pumped out of the second reactor at the same rate as the in-going feed to the second reactor to maintain the content in the second reactor constant. The reaction material from the second reactor is then transferred to a multistage column reactor. The product from the second reactor has a degree of conversion of about 50% with an unreacted sucrose level of about 1 weight %.

EXAMPLE 2

The first step reaction product from Example 1 is pumped continuously into a multistage column reactor, together with a second portion of fatty acid methyl esters in an amount providing a total fatty acid methyl ester:sucrose molar ratio of about 11:1. Additional potassium carbonate is added to the incoming reaction material to provide a total potassium carbonate:sucrose ratio of about 0.2:1. The column is designed to approximate plug flow, and to provide intimate contact between the stripping gas and the reaction liquid. The column consists of a section of glass pipe approximately 6 inches in diameter and 48 inches long. Seven plates are placed in the column at equal intervals to segment the column into seven sections. Each plate has a center hole about 1 inch in diameter. Each section has a 6-blade turbine type agitator, operated at about 600 rpm. The agitator diameter is approximately one-half the diameter of the column.

The first step reaction product from Example 1 is fed into the top of the column and travels downward through the column through the center hole of each of the successive section plates. Nitrogen is introduced at the bottom of the column and travels upward through the column, through the center holes, counter current to the liquid flow. In each segment, the nitrogen is dispersed into the liquid by radial shear agitation provided by the agitators to produce very small bubbles, approximately 2 mm in average diameter. The partial pressure of methanol in the nitrogen gas in the bottom section of the column is about 1 mm Hg. The nitrogen strips the methanol by-product from the reaction mixture, and proceeds upward through the column propelled by buoyant forces, from section to section. The nitrogen is exhausted from the column when it reaches the top. The reaction product is pumped from the bottom of the column. The reaction is operated at about 135° C. The reactor pressure at the top of the column is about atmospheric, and the reactor pressure is about 0.5 psig above atmospheric pressure at the bottom of the column. The weight ratio of nitrogen to the incoming liquid feed is about 2:1, and the average residence time of the liquid in the column is about 2 hours. This reaction gives a product having a sucrose degree of conversion of approximately 95.3% and containing about 63% sucrose octaester.

EXAMPLE 3

This example describes the procedure to measure the Peclet number of the reactor column in Example 2. The Peclet number is a quantitative measure of plug flow in a reaction system. Peclet number can be measured by a number of different methods. Particularly useful in an experimental environment is the method described by O. Levenspiel, *Chemical Reaction Engineering*, pp. 253–314, using tracers. A tracer pulse is injected into the feed stream going into the reactor, and the concentration of the tracer is continuously monitored as it exits the reactor. From this tracer data, Peclet number can be calculated. A Peclet number of zero indicates complete backmixing, no plug flow. A Peclet number of infinity indicates perfect plug flow. In Example 2, about 50 grams of soybean triglyceride are injected as a tracer pulse into the feed stream to the column, once the reactor has reached mass balance and steady rate of inlet and outlet flows. From this tracer data, the Peclet number is calculated to be about 2.5.

EXAMPLE 4

This example uses a similar reaction column as Example 2 except that the column has 14 plates that divide the column into 14 sections. Each section is approximately one-half the height of the sections in Example 2, and the total reaction height of the column is the same. The purpose of dividing the column into more segments is to more nearly approximate plug flow than in Example 2. The agitator and plate design in this example are the same as in Exhibit 2. Reaction material from the first step of the reaction (Example 1) is pumped continuously into the column reactor along with the second portion of fatty acid methyl esters to provide a total fatty acids methyl ester:sucrose molar ratio of about 11:1. Additional potassium carbonate is added to the incoming reaction material to provide a total potassium carbonate:sucrose ratio of about 0.2:1. Reaction conditions in this example are similar to Example 2, i.e., 135° C., a weight ratio of nitrogen to feed of about 2:1, and an average liquid residence time of about 2 hours. This reaction gives a product in which the sucrose is approximately 98.5% esterified, containing about 88% sucrose octaester. The higher conversion to sucrose octaester is a result of the higher degree of plug flow in this design.

EXAMPLE 5

This example describes the use of a reaction column to perform both stages of the transesterification reaction, i.e., the initial esterification of sucrose to sucrose lower esters, and the further reaction to a high degree of esterification. A column is constructed that contains two sections, one on top of the other. The top section is designed for the initial esterification. This section consists of an approximately 9-inch diameter, 24-inch long glass column divided into 2 sections by two plates similar in design to the plates employed in the previous examples, except that the plates are about 9-inches in diameter. Each plate has a center hole about 1-inch in diameter. Each segment is about 12 inches high and has a 6-bladed turbine agitator that is approximately one half the diameter of the column. Fewer segments in this section of the column lead to more backmixing, which is desirable in the initial sucrose esterification, as previously described. The lower section of the column is identical to that described in Example 4, i.e., 6-inches in diameter and divided into 14 sections. The lower section is designed for a second stage of the reaction, i.e., the esterification of sucrose lower esters to sucrose polyesters. A single agitator shaft runs through both sections of the column, and turns all of the agitators simultaneously. Both sections have heating mantles.

Reaction material for the first stage of the reaction is fed into the top of the column and travels downward through the column through the center hole of each of the successive section plates. The feed material comprises sucrose, potassium carbonate, and cottonseed fatty acid methyl esters in the same molar ratios as in Example 1. Potassium stearate is not employed in this example. Sucrose is emulsified into the methyl esters by sucrose mono-, di-, and triesters that are present in the top section of the column. The reaction material flows downward by gravity from the top section of the column to the narrower lower section of the column. At the top of the narrower lower section of the column, additional cottonseed fatty acid methyl esters are added to raise the molar ratio of total methyl esters to initial sucrose to about 11:1. Additional potassium carbonate is added to raise the molar ratio of total potassium carbonate to initial sucrose to about 0.2:1. The resulting liquid mixture flows down the lower section of the column for further reaction. Nitrogen is introduced at the bottom of the column and travels upward through the column, through the center holes, counter current to the liquid flow. In each segment, the nitrogen is dispersed into the liquid by the agitators to produce very small bubbles, approximately 2 mm diameter average. The partial pressure of methanol in the nitrogen gas in the bottom section of the column is about 1 mm Hg. The pressure at the top of the column is approximately atmospheric, and the pressure at the bottom of the column is about 0.6 psig. This reaction yields a product in which the sucrose degree of conversion is approximately 94.4%.

EXAMPLE 6

This example uses a similar reaction column as Example 2, except that the plate design is different. In this example, each plate has several small holes that allow the nitrogen gas to pass upwardly through the plate, and overflow weirs and downcomer tubes that allow the liquid to flow from one segment to another. This design is similar to the tray design common in many distillation column applications. The plates do not have a center hole as described in Example 2. Under normal operating conditions only gas moves upward through the small holes, and only liquid moves downwardly through the overflow weirs and downcomers. This separation of the gas and liquid transfer between stages, rather than combined through a common opening as in Example 2, is designed to limit liquid backmixing, and therefore provide greater plug flow as compared with the column in Example 2. The holes for the inert gas are about ³⁄₁₆-inch in diameter, and comprise about 5% of the total surface area of the plate. There are seven segments in the column, and the column has the same overall reactor height as in Example 2. The reactions conditions are similar to those of Example 2: about 600 rpm agitator speed, a gas to liquid feed weight having a sucrose degree of conversion of about 97.5% and containing about 80% sucrose octaester. The higher conversion to sucrose octaester is a result of the higher degree of plug flow in this design. The Peclet number for the reactor in this example is approximately 9.

EXAMPLE 7

This example uses the same reactor design and conditions as Example 5, with the exception of agitator speed. Agitator speed determines the degree of dispersion of the nitrogen in the liquid, and therefore how much liquid/vapor surface area is available for the mass transfer of methanol from the liquid to the stripping gas. Three separate reactions are performed using the same conditions for the agitator speed. Specifically, the agitator speed for the three reactions is 300 rpm, 500 rpm, and 600 rpm, respectively. The results of these three reactions are as follows:

| Agitator RPM | % Esterification | % Sucrose Octaester |
| --- | --- | --- |
| 300 | 95.6 | 65 |
| 500 | 96.3 | 70 |
| 600 | 97.8 | 82 |

This example shows that higher agitation speeds lead to improved conversion as a result of improved contact between the liquid and the gas.

EXAMPLE 8

This example uses the same reactor column as Example 4. The purpose of this example is to show the effect of Aeration Number (Ae) on conversion. Aeration number is a dimensionless number that can be determined for any column size, regardless of scale. Aeration number (Ae) is calculated by the following formula: $Ae = $(Inert gas volumetric flow rate)/(Agitator speed)/(Agitator diameter)$^3$. Lower aeration numbers are indicative of better dispersion of the inert gas into the liquid by the agitator. This increases the liquid/vapor surface area available for the mass transfer alcohol by-product, i.e., methanol, from the liquid to the stripping gas. Higher Aeration numbers are indicative of less efficient dispersion of the gas into the liquid. Two separate reactions are performed, each the same except that the agitator speed is varied to change the average Aeration number. The results of these two reactions are as follows:

| Aeration number | % Esterification | % Sucrose Octaester |
| --- | --- | --- |
| 0.7 | 96.4 | 71 |
| 0.3 | 98.5 | 88 |

Lower Aeration numbers will generally result in higher conversion to octaester, all other factors being equal. The Aeration number can also be changed by changing the agitator diameter. A larger agitator diameter will result in a smaller Aeration number, leading to a higher conversion to sucrose octaester.

EXAMPLE 9

This example uses a glass column reactor, 12-inches in diameter and 72-inches in length. The section plates are similar to the plates in Example 5, i.e., small holes in the plates allow upward travel of the gas, while liquid flow is directed through overflow weirs and downcomer tubes. There are six section plates in this column, and each section has a six-bladed turbine agitator having a diameter approximately one-half the diameter of the column. The molar ratio of total fatty acid methyl esters to sucrose in the column is 11:1. Two separate reactions are run in this column, one having a lower agitation rate, but higher gas/liquid ratio, the second having a higher agitation rate, but a lower gas/liquid ratio. The liquid residence time for each reaction is approximately 2 hours. The results of these two reactions are as follows:

| Agitator rpm | Gas/Liquid weight ratio | % Esterification | % Sucrose Octaester |
| --- | --- | --- | --- |
| 300 | 3:1 | 96.8 | 74 |
| 380 | 1.5:1 | 96.3 | 70 |

The conversions are very similar, even though the first reaction used twice the gas liquid ratio as the second reactor. This example shows that efficient dispersion of the gas in the reaction liquid can lead to reduced levels of inert gas required to drive the reaction to high conversion.

EXAMPLE 10

This example uses a similar reaction column as Example 6, except that the downcomer tubes have valves on them to regulate the flow of liquid between each segment. The downcomers can be either internal or external to the column. The same sieve tray plate design is used to direct the flow of gas upward between each segment. This design retains the plug flow advantages of the system of Example 6, and also provides operability advantages in startup, shutdown, and steady state operation control.

For startup and shutdown, the column employed in this example is advantageous in that no weeping or dumping of liquid from the trays occurs, and hence greater equipment reliability and product yield is obtained. This is accomplished by ensuring that while the column is partially fuill, all of the gas is directed up through the sieve trays, and none is bypassed up through any downcomer which does not have liquid flowing through it. Specifically, during start up, the valve for the downcomer on each stage is opened only after the liquid level in that stage is sufficient to flood the downcomer with liquid and thereby prevent any undesirable bypassing of gas upwardly through the downcomer rather than through the sieve tray. For steady state operation, better process control is obtained by having adjustable liquid residence time in each segment. This can be accomplished by using modulating control valves on each downcomer, which valves are automatically opened or closed to maintain a particular liquid level in each segment.

If external downneomers are used between each segment, additional hardware can be added to aid in processing the liquid, including, but not limited to, pumps, heat exchangers, and/or separators, and the like.

EXAMPLE 11

This example uses a similar reaction column as Example 6. The first stage reaction is conducted in a manner similar to that described in Example 1 except that the residual sucrose level in the first stage reaction product material is less than about 0.5 weight %. Reaction material from the first stage of the reactor is pumped continuously into a column reactor along with additional fatty acid methyl esters to bring the total fatty acid methyl ester:sucrose ratio to about 13:1. Additional potassium carbonate is added to the incoming reaction material to bring the total potassium carbonate:sucrose ratio to about 0.26:1. The reaction is conducted at about 275° F., at about atmospheric pressure at the top of the column, and at about 5 psig above atmospheric pressure at the bottom of the column. The weight ratio of nitrogen stripping gas to the incoming liquid feed is about 2:1, and the average residence time of the liquid in the column is about 2 hours. In this example the agitation is reduced to about 50 rpm. This reaction gives a product in which the sucrose is approximately 96.9% esterified, containing about 75% sucrose octaester.

The specific and preferred embodiments provided herein are set forth to illustrate the invention and are not intended to limit the scope of the methods of the present invention. Additional embodiments and advantages within the scope of the claimed invention will be apparent to one of ordinary skill in the art.

What is claimed is:

1. A process for the synthesis of polyol fatty acid polyester by transesterification of polyol, comprising reacting polyol with a first portion of fatty acid lower alkyl ester to provide a first step reaction product in which substantially all of the polyol is reacted with at least one fatty acid lower alkyl ester, providing a multistage column wherein each stage is separated from an adjacent prior stage by a segment plate and each segment plate is provided with at least one passage allowing transfer of a liquid in a first direction between adjacent stages and with at least one passage allowing transfer of a gas in a second direction between adjacent stages, the second direction being counter current to the first direction, providing the first step reaction product and a second portion of fatty acid lower alkyl ester to the column to cause reaction of the first step reaction product and fatty acid lower alkyl ester and form a liquid mixture comprising partially esterified polyol, fatty acid lower alkyl ester and lower alkyl alcohol by-product, passing the liquid mixture in the first direction between adjacent stages through the column whereby further reaction of partially esterified polyol and fatty acid lower alkyl ester occurs to form a polyol polyester product, and feeding an inert gas through the column in the second direction between adjacent stages, counter current to the flow of the liquid mixture in the first direction, with agitation providing radial shear to increase gas-liquid contact between the inert gas and the liquid mixture, whereby the lower alkyl alcohol by-product of the transesterification reaction is transferred from the liquid mixture to the inert gas.

2. A process as defined by claim 1, wherein each stage of the column includes at least one agitator providing radial shear to increase contact surface area between the liquid mixture and the inert gas within the respective stages.

3. A process as defined by claim 2, wherein each agitator includes from about 6 to about 12 radially extending, agitator blades rotating around a center axis of the stage.

4. A process as defined by claim 3, wherein the radially extending agitator blades are concavely curved in the direction of rotation.

5. A process as defined by claim 1, wherein at least one stage of the column is provided with at least one baffle extending between adjacent segment plates defining the stage, the baffle providing increased contact surface area between the liquid mixture and the inert gas.

6. A process as defined by claim 1, wherein the passage allowing transfer of a liquid in a first direction between adjacent stages comprises a plurality of overflow/downcomer tubes, and further wherein the liquid mixture flows from an overflow portion of a tube in one stage into a downcomer portion of the tube in an adjacent stage.

7. A process as defined by claim 6, wherein the passage allowing transfer of a gas in a second direction between adjacent stages comprises a plurality of sieve holes provided in each segment plate.

8. A process as defined by claim 1, wherein the column comprises at least 3 stages.

9. A process as defined by claim 1, wherein the column comprises at least about 4 stages.

10. A process as defined by claim 1, wherein the reactions are conducted at a temperature in the range of from about 120° C. to about 180° C.

11. A process as defined by claim 1, wherein the reactions in the column are conducted at a pressure of not less than atmospheric pressure.

12. A process as defined by claim 1, wherein the pressure, at the top of the column is in the range of from about 760 to about 2500 mm Hg.

13. A process as defined by claim 1, wherein the pressure at the top of the column is in the range of from about 760 to about 1100 mm Hg.

14. A process as defined by claim 1, wherein the polyol comprises sucrose.

15. A process as defined by claim 1, wherein the fatty acid lower alkyl ester comprises methyl esters of soybean, palm, coconut, fully hydrogenated rapeseed or cottonseed oils, or mixtures thereof.

16. A process as defined by claim 1, wherein the a catalyst comprising a carbonate, bicarbonate, alkoxide or hydride of sodium or potassium, or mixtures thereof is employed in the reactions.

17. A process as defined by claim 1, wherein the inert gas is nitrogen.

18. A process as defined by claim 1, wherein the weight ratio of inert gas feed to liquid feed to the multistage column is less than about 3:1.

19. A process as defined by claim 1, wherein the weight ratio of inert gas feed to liquid feed to the multistage column is less than about 2:1.

20. A process as defined by claim 1, wherein the multistage column, in operation, has an aeration number less than about 2.0.

21. A process as defined by claim 1, wherein the partial pressure of lower alkyl alcohol in a last stage of the multistage column from which the polyol polyester product is removed is less than about 2 mm Hg.

22. A process as defined by claim 1, wherein liquid material residence time in the multistage column is less than about 3 hours.

23. A process as defined by claim 1, wherein the reaction of the first step reaction product of partially esterified polyol with the second portion of fatty acid lower alkyl ester is conducted in the column in the absence of an emulsifier.

24. A process as defined by claim 1, wherein a third portion of fatty acid lower alkyl ester is fed into the column at a stage which is intermediate the ends of the column.

25. A process as defined by claim 1, further comprising removing a liquid containing polyol polyester product from the column.

26. A process as defined by claim 25, wherein the polyol is sucrose and wherein the polyol polyester product contains at least 70 weight percent octaester.

27. A process as defined by claim 25, wherein the polyol polyester product has a degree of conversion of at least 95%.

28. A process as defined by claim 1, comprising the further steps of removing the inert gas containing the lower alkyl alcohol by-product from the column, removing substantially all of the lower alkyl alcohol from the inert gas, and recycling the inert gas to the column.

29. A process as defined by claim 28, wherein the step of removing substantially all of the lower alkyl alcohol from the inert gas comprises cooling the inert gas containing the lower alkyl alcohol and passing the cooled product through an absorbent material.

30. A process as defined by claim 29, wherein the recycled inert gas has a lower alcohol partial pressure of less than about 10 mm Hg.

31. A process as defined by claim 1, wherein the first step reaction product comprises unreacted polyol in an amount of less than about 2 weight percent.

32. A process as defined by claim 1, wherein the first step reaction product comprises unreacted polyol in an amount of less than about 1 weight percent.

33. A process as defined by claim 1, wherein the polyol is reacted with the first portion of fatty acid lower alkyl ester in a batch reactor.

34. A process as defined by claim 1, wherein the polyol is reacted with the first portion of fatty acid lower alkyl ester in a continuous stirred tank reactor.

35. A process as defined by claim 1, wherein the polyol is reacted with the first portion of fatty acid lower alkyl ester in two continuous stirred tank reactors arranged in series.

36. A process as defined by claim 1, wherein the polyol is reacted with the first portion of fatty acid lower alkyl ester in a multistage column reactor.

37. A process as defined by claim 1, wherein the first step reaction product comprises a degree of conversion of at least about 25%.

38. A process as defined by claim 6, wherein the downcomer tubes are external to the column.

* * * * *

UNITED STATES PATENT AND TRADEMARK OFFICE
CERTIFICATE OF CORRECTION

PATENT NO. : 5,945,529
DATED : August 31, 1999
INVENTOR(S) : Patrick J. Corrigan et al It is certified that error appears in the above-identified patent and that said Letters Patent is hereby corrected as shown below:

Column 18, line 36, change "wherein the a catalyst" to --wherein a catalyst--.

Signed and Sealed this

Sixteenth Day of May, 2000

Attest:

Q. TODD DICKINSON

*Attesting Officer*   *Director of Patents and Trademarks*